United States Patent [19]
Yamagishi et al.

[11] Patent Number: 5,229,935
[45] Date of Patent: Jul. 20, 1993

[54] 3-DIMENSIONAL IMAGE DISPLAY APPARATUS CAPABLE OF DISPLAYING A 3-D IMAGE BY MANIPULATING A POSITIONING ENCODER

[75] Inventors: Ichiro Yamagishi; Hiroyuki Urushiya, both of Tokyo, Japan

[73] Assignee: Kabushiki Kaisha Toshiba, Kanagawa, Japan

[21] Appl. No.: 556,725

[22] Filed: Jul. 25, 1990

[30] Foreign Application Priority Data

Jul. 31, 1989 [JP] Japan ................... 1-198421

[51] Int. Cl.⁵ ............................................. G06F 15/42
[52] U.S. Cl. ........................ 364/413.22; 364/413.13; 395/128
[58] Field of Search .............. 364/413.13, 413.14, 364/413.22; 395/119, 124, 126, 128; 378/901

[56] References Cited

U.S. PATENT DOCUMENTS

| | | | |
|---|---|---|---|
| 4,105,922 | 8/1978 | Lambert et al. | 364/413.22 |
| 4,334,222 | 6/1982 | Kelley et al. | 340/870.29 |
| 4,560,983 | 12/1985 | Williams | 340/825 |
| 4,563,740 | 1/1986 | Blake et al. | 364/413.22 |
| 4,809,065 | 2/1989 | Harris et al. | 358/88 |
| 4,825,365 | 4/1989 | Inoue | 364/413.19 |
| 4,839,805 | 6/1989 | Pearson, Jr. et al. | 364/413.14 |
| 4,852,002 | 7/1989 | Klausz | 364/413.13 |
| 4,879,668 | 11/1989 | Cline et al. | 364/413.22 X |
| 5,042,077 | 8/1991 | Burke | 382/51 |

OTHER PUBLICATIONS

SPIE, vol. 173, *Application of Optical Instrumentation in Medicine* VII (1979), Heck "Display System for Computed Tomographic (CT) Images", pp. 244-247.

*Primary Examiner*—Roy N. Envall, Jr.
*Assistant Examiner*—David Huntley
*Attorney, Agent, or Firm*—Finnegan, Henderson, Farabow, Garrett & Dunner

[57] ABSTRACT

In an X-ray three-dimensional image display apparatus, a rotary encoder unit is employed which determines a window level and width of a two-dimensional image, and furthermore determines both upper and lower threshold limits in an X-ray CT (computerized tomographic) value of an X-ray tomographic image. The three-dimensional image display apparatus further includes a 3-dimensional image construction unit for constructing the 3-dimensional image from image data of a plurality of X-ray CT slices based upon the determined upper and lower limit values of the X-ray value. The rotary encoder unit includes D-type flip-flops which provide pulse signals to pulse counters.

7 Claims, 5 Drawing Sheets

3-DIMENSIONAL IMAGE DISPLAY APPARATUS CAPABLE OF DISPLAYING A 3-D IMAGE BY MANIPULATING A POSITIONING ENCODER

BACKGROUND OF THE INVENTION

1. Field of the Invention

The present invention generally relates to a three-dimensional image display apparatus capable of displaying medical images such as X-ray CT (computerized tomography) images and MRI (magnetic resonance imaging) images as 3-D images. More specifically, the present invention is directed to a 3-D image display apparatus that immediately forms 3-D images, e.g., a surface image of a patient, from a plurality of X-ray CT images by simply manipulating a positioning encoder.

2. Description of the Related Art

Generally speaking, in conventional 2-dimensional X-ray CT imaging apparatuses, the positioning encoder unit, for instance, a rotary encoder is employed so as to set the window level/width of the acquired two-dimensional CT image with respect to the CT value thereof. Furthermore, to display the three-dimensional image, e.g., surface images of organs, bones and blood vessels of a patient, by these CT imaging apparatuses, a plurality of acquired CT image data must be processed by way of the known voxel method, and also both the upper and lower threshold levels must be determined in order to extract each CT value of the relevant CT imaging region by operating the keyboard. In other words, to perform the voxel method for the plurality of CT image data, such a threshold level setting operation must be carried out with respect to all of the acquired CT images, which may require cumbersome keyboard operations.

Moreover, the function of the positioning encoder employed in the conventional X-ray CT imaging apparatus is to merely determine the CT value of the respective two-dimensional CT images, not to determine the threshold levels of the 3-dimensional image.

As a result, since the voxel data must be formed for each of the acquired X-ray CT images, a lengthy waiting time is necessarily required for finally displaying the desired 3-D image. Moreover, when a sort of the desired 3-D image is varied from the bone to the organs, for example, this drawback, namely length waiting time, is further emphasized.

The present invention has been made in an attempt to solve the above-described drawbacks of the conventional 3-D image display apparatuses, and therefore has an object to provide a 3-D image display apparatus capable of readily changing the region of the object under medical examination to be imaged with a simple operation, and also of immediately displaying the 3-D image of the desirable imaging region.

Another object of the invention is to provide a 3-D image display apparatus employing a positioning encoder unit capable of determining the threshold levels of the 3-D image.

SUMMARY OF THE INVENTION

To achieve the above-described objects, a three-dimensional image display apparatus according to the present invention comprises:

means for setting a region of a tissue of a biological body under medical examination, to be imaged as a three-dimensional image, in response to an operation of a positioning device used to determine a window value of a two-dimensional image;

means for constructing the three-dimensional image corresponding to the region of the biological body's tissue to be imaged based upon a plurality of computerized tomographic image data; and, means for displaying the three-dimensional image constructed by the 3-D (dimensional) image constructing means.

BRIEF DESCRIPTION OF THE DRAWINGS

For a better understanding of the above objects of the present invention, reference is made to the following detailed description of the invention to be read in conjunction with the following drawings, in which.

DETAILED DESCRIPTION OF THE PREFERRED EMBODIMENTS

Overall Arrangement of 3-D Image Display Apparatus

Figure 1:
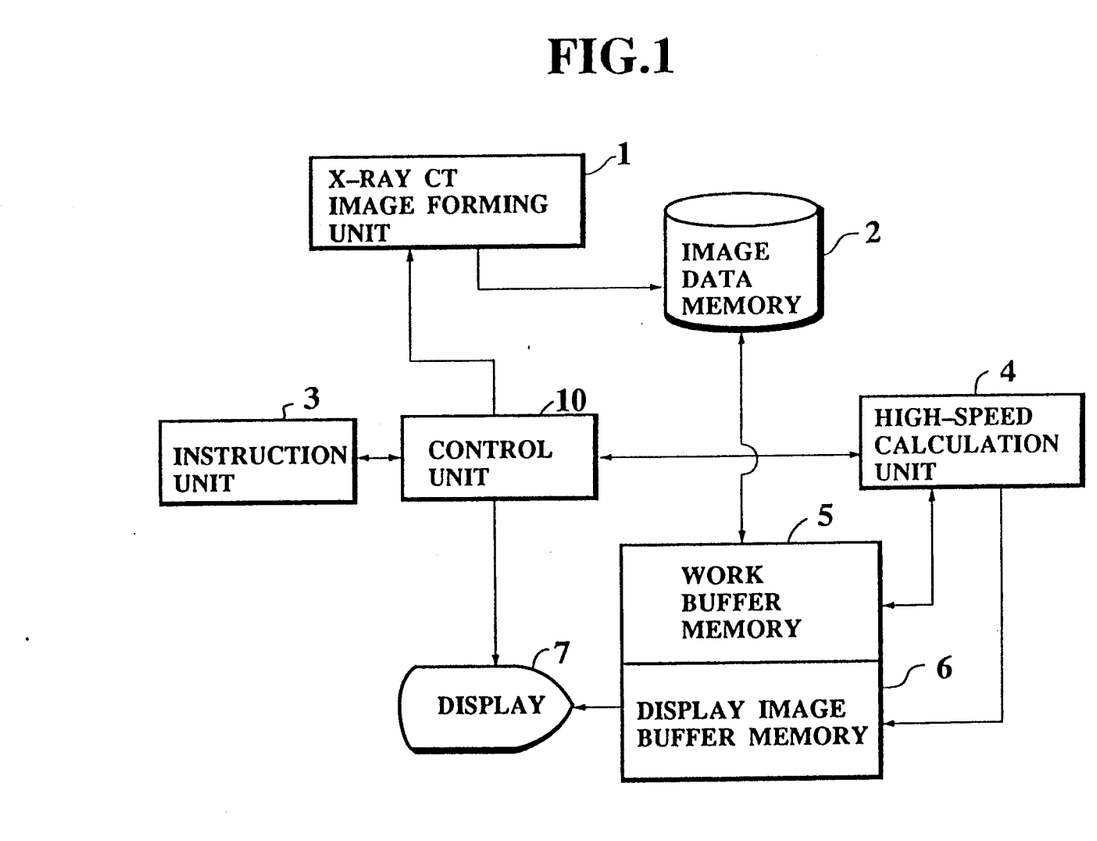
FIG. 1 is a schematic block diagram of a 3-D image display apparatus according to a preferred embodiment of the present invention.

In FIG. 1, there is shown an X-ray 3-D (dimensional) image display apparatus according to an preferred embodiment of the present invention. This X-ray 3-D image display apparatus may display not only a 3-dimensional image of an object (not shown in detail) under medical examination but also an X-ray CT (computerized-tomographic) image thereof. The X-ray 3-D image display apparatus is mainly constructed of: an X-ray CT image forming unit 1 for acquiring a plurality of CT images of the object under medical examination to form X-ray CT image data; an image data memory 2 for storing the X-ray CT image data therein; an instruction unit 3 for instructing various functions of this display apparatus (which will be discussed later; a high-speed calculation unit 4 for calculating a plurality of X-ray CT image data at high speed which have been read out from the image data memory 2 and also have been temporarily stored in a work buffer memory 5; a display image buffer memory 6 for temporarily storing desirable 3D image data of the object instructed by the instruction unit 3 and calculated by the high-speed calculation apparatus 4; a display unit 7 for displaying the desirable 3D image in response to the 3D image data temporarily stored in the display image buffer memory 6; and a control unit 10 for controlling each of the above-described circuit units.

Detailed Arrangement of Instruction Unit/High-Speed Calculation Unit

Since both the above-described instruction unit 3 and high-speed calculation unit 4 constitute features of this preferred embodiment, more detailed arrangements will now be described with reference to FIGS. 2A, 2B, 3A and 3B.

Figure 2A:
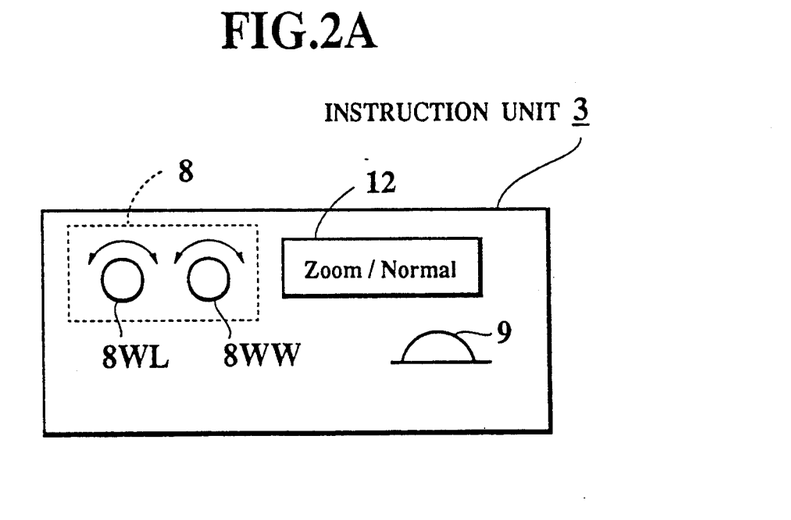
FIGS. 2A and 2B represent a positioning encoder unit employed in the display apparatus shown in FIG. 1.

FIG. 2A illustrates a front panel of the instruction unit 3. This instruction unit 3 is mainly constructed of a positioning encoder unit 8, a track ball 9, and a display mode changing key 12. Since the functions of the track ball 9 and display mode changing key 12 are known to those having ordinary skill in the art, no further explanation thereof is made in the following description.

Figure 2B:
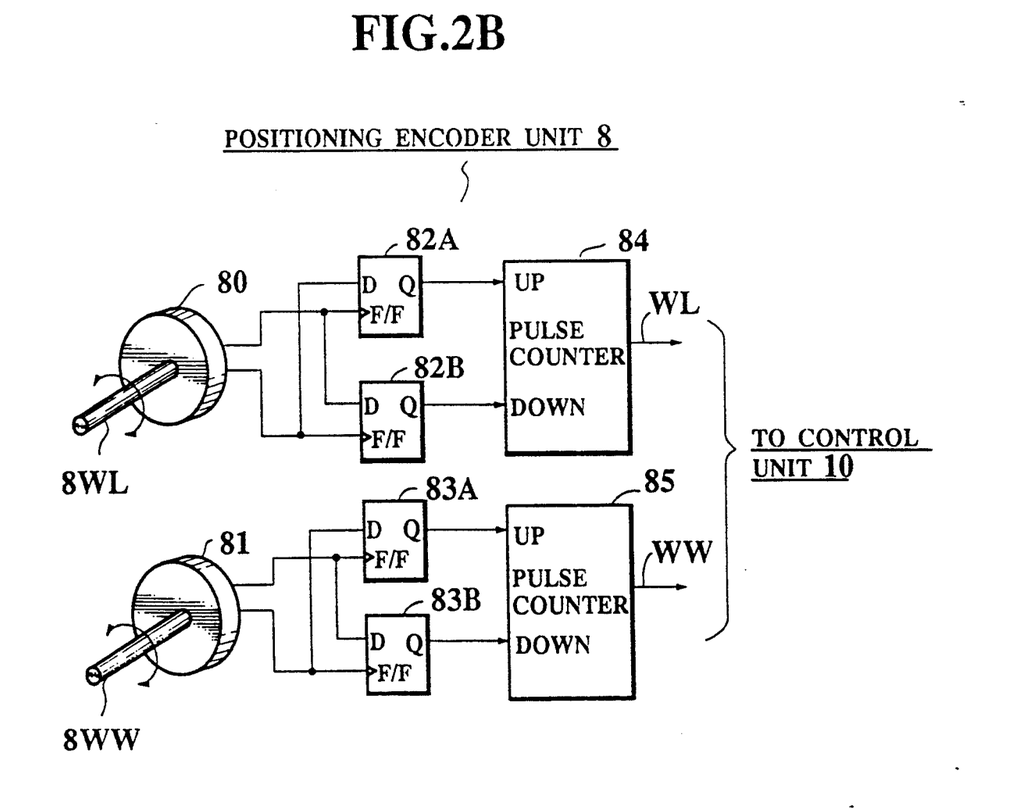

The function of the positioning encoder unit 8 will now be described with reference to FIGS. 2A and 2B. In FIG. 2B, there is shown an internal circuit arrangement of the positioning encoder unit 8. This positioning encoder unit 8 is mainly arranged by two sets of rotary encoder/pulse counter circuit arrangements. To set a center value "WL" of the above-described threshold level range as represented in FIG. 4, a first rotary encoder/pulse counter circuit arrangement is employed. The first rotary encoder/pulse counter circuit arrangement includes a first rotary encoder 80 having a first rotary knob 8WL; two sets of D type flip-flops 82A and 82B coupled to the outputs of the first rotary encoder 80 to receive encoder pulses derived therefrom; and a first pulse counter 84 having an up count terminal and a down count terminal, into which the outputs from these flip-flops 82A and 82B are supplied. By rotating the first knob 8WL of the rotary encoder 80, the first pulse counter 84 outputs a first positioning signal corresponding to a center setting signal for setting the center value "WL".

On the other hand, the second rotary encoder/pulse counter circuit arrangement includes: a second rotary encoder 81 having a second rotary knob 8WW; two sets of D type flip-flops 83A and 83B coupled to the outputs of the second rotary encoder 81 to receive encoder pulses derived therefrom; and a second pulse counter 85 having an up count terminal and a down count terminal, into which the outputs from these flip-flops 83A and 83B are furnished. Similarly, by rotating the second knob WW of this second rotary encoder 81, the second pulse counter 85 outputs a second positioning signal corresponding a width setting signal for setting the width "WW" of the threshold level range.

Figure 3A:
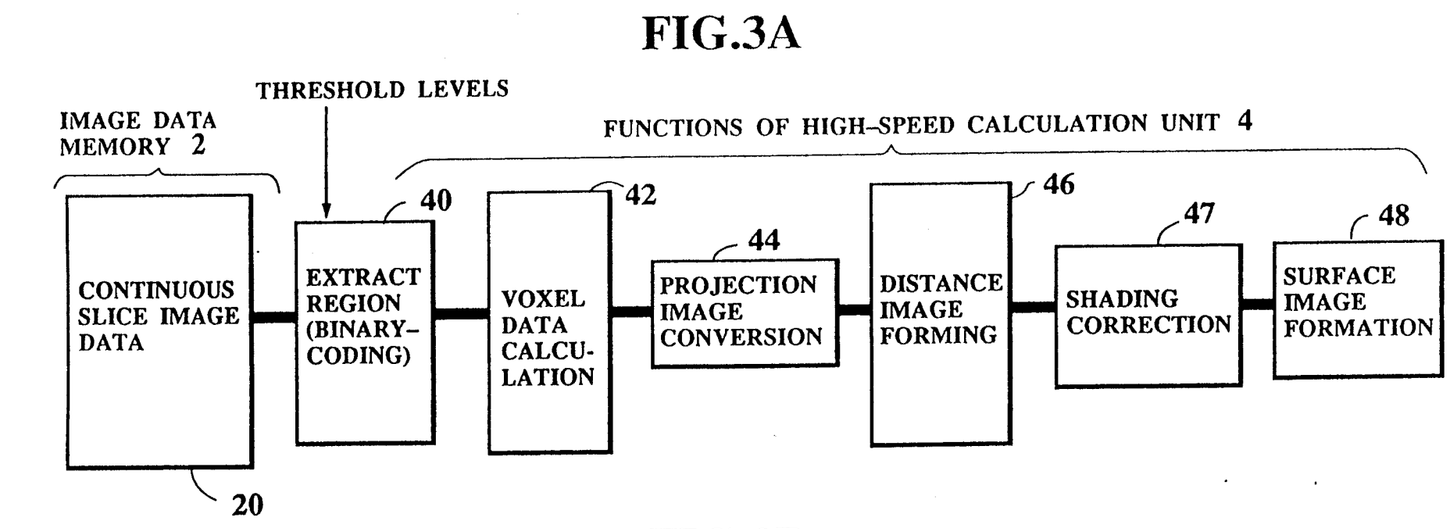
FIGS. 3A and 3B pictorially represent the functions of the high-speed calculation unit employed in the display apparatus shown in FIG. 1.
Figure 3B:
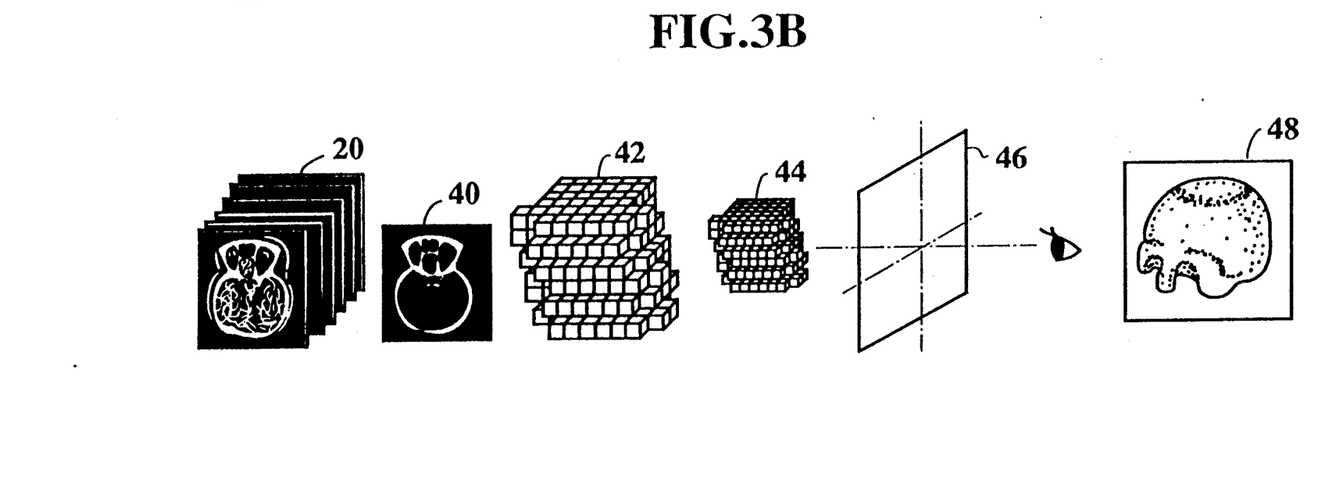

FIG. 3A graphically represents a formation of a 3-D surface image by the high-speed calculation unit 4, whereas FIG. 3B pictorially illustrates how to produce such a 3-D surface image by the high-speed calculation unit 4. It should be noted that each of the processing steps 40 through 48 as defined in FIG. 3A corresponds to each of the pictorial steps as shown in FIG. 3B except for a shading correction step 47.

As represented in FIG. 3A, image data 20 of a plurality of continuous image slices is stored in the image data memory 2 shown in FIG. 1. The continuously acquired image data 20 is first binary-coded, thereby obtaining binary-coded image data 40. In other words, the desired region of the image slices is extracted. Thereafter, voxel data 42 is calculated from the binary-coded image data 40. The resultant voxel data 42 is converted into projection image data 44. Subsequently, the projection image data 44 is processed to form distance image data 46. Then, the distance image data 46 is shading-corrected at the shading correction step 47. Finally, a desired surface image of a head portion of a patient is obtained at a surface image formation step 48 in this preferred embodiment.

Figure 4A:
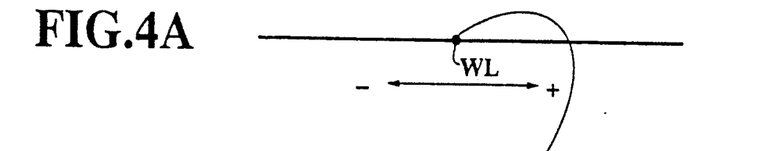
FIGS. 4A and 4B and 5A to 5C schematically illustrate the threshold level setting operations by the positioning encoder shown in FIG. 3B; and, FIG. 6 shows display conditions of the display unit 7 employed in the display apparatus represented in FIG. 1.
Figure 4B:
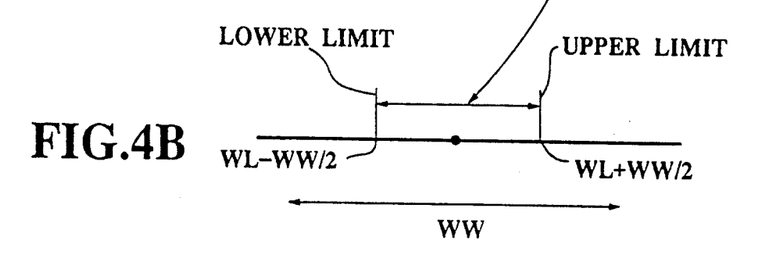

More specifically, when the first rotary knob 8WL of the first rotary encoder 80 is rotated along the arrowed direction as represented in FIG. 2B, the center "WL" of the threshold level is varied within a range, as illustrated in FIG. 4A. Also when the second rotary knob 8WW of the second rotary encoder 81 is rotated along another arrowed direction, the width "WW" of this threshold level is similarly changed within another range, as illustrated in FIG. 4B. That is, both a lower limit (WL−WW/2) and an upper limit (WL+WW/2) are determined by setting the second rotary knob 8WW of the second rotary encoder 81.

As previously explained, in accordance with the preferred embodiment, while the first and second rotary knobs 8WL and 8WW of the first and second rotary encoders 80 and 81 are rotated along the predetermined rotation directions, not only can both the window level and window width be set when the normal two-dimensional image is observed, but also the range of the threshold levels (see FIGS. 4A through 5A) may be readily set which is required so as to determine the region of the tissue of the object under medical examination in the control unit 10.

Overall Operation of X-ray 3-D Image Display Apparatus

Referring back to FIG. 1, an overall operation of the X-ray 3-D image display apparatus will now be described.

Assuming now that a plurality of X-ray CT images have been acquired and formed by the X-ray CT image forming unit 1 and thereafter stored into the image data memory 2, the positioning encoder unit 8 shown in FIGS. 2A and 2B is operated to set the above-described range of threshold levels. As a result, the region of the object's tissue is determined under control of the control unit 10 in response to the outputs (i.e., level setting signals) from the positioning encoder unit 8. At the same time, image data of a plurality of X-ray CT slices is read out from the image data memory 2 and transferred via the work buffer memory 5 to the high-speed calculation unit 4.

In response to this image data, the high-speed calculation unit 4 performs the above-described data process. Subsequently, the desired three-dimensional image corresponding to the above-determined range of threshold levels is formed in the high-speed calculation unit 4 and temporarily stored in the display image buffer memory 6 under control of the high-speed calculation apparatus 2. Thus, the 3-D image temporarily stored in the display image buffer memory 6 is displayed on the display unit 7. On the other hand, every time the image data of the plurality of images is successively selected by manipulating the track ball 9 on the instruction unit 3 shown in FIG. 2A, the binary-coded images 40, represented in FIG. 3B, corresponding to the above-described range of threshold levels with respect to the selected slice images are similarly constructed in the high-speed calculation unit 4.

Figure 5A:
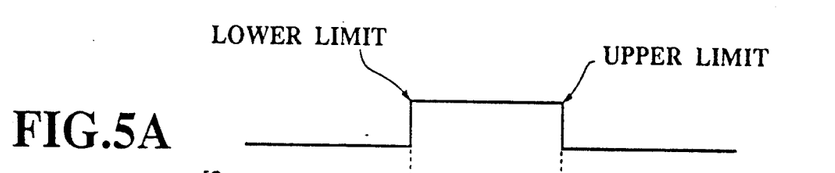
Figure 5B:
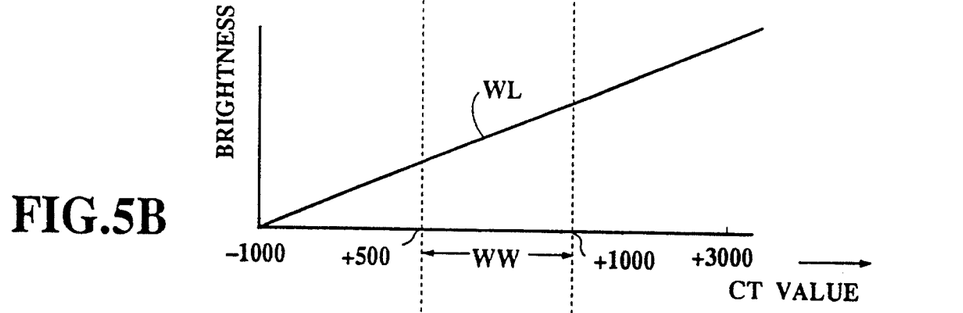
Figure 5C:
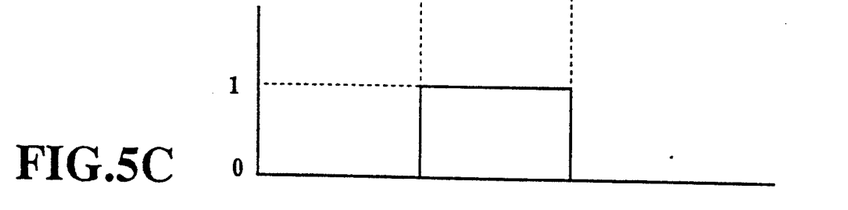

Therefore, when the positioning encoder unit 8 shown in FIGS. 2A and 2B is operated to set the threshold level range as represented in FIGS. 4A, 4B, and 5A, the CT values having +500 (lower limit CT value) and +1,000 (upper limit CT value) are determined (see FIG. 5B), and then both the binary-coded image and three-dimensional image are formed by the high-speed calculation unit 4 based upon the determined CT values.

Figure 6:
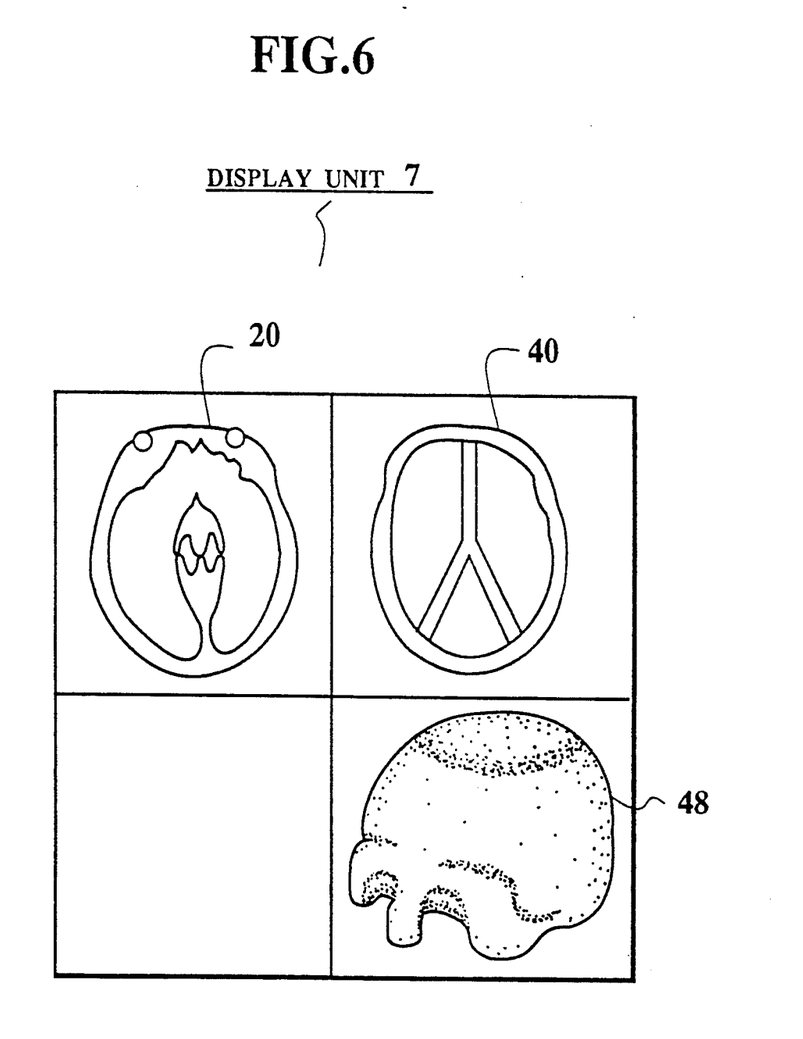

At a result, the normal X-ray tomographic image 20 of the patient's head portion is displayed on an upper left quarter portion of the display unit 7, as represented in FIG. 6, by operating the track ball 9 provided on the instruction unit 7, the binary-coded image 40 corresponding to the above-determined range of the threshold levels is displayed on an upper right quarter portion thereof, and, furthermore, the desired 3-D image 48 (i.e., head bone) is displayed on a lower right quarter portion thereof.

One advantage of the present invention is that the above-described three relevant images 20, 40 and 48 can be simultaneously displayed on the same screen of the display unit 7, and also while observing the range of the binary-coded image 40 on the scanning slice planes, the desired three-dimensional image 48 such as a bone and an outer skin may be monitored at this observation time. A transparent image may be displayed instead of a surface image.

MODIFICATIONS

As apparent from the foregoing descriptions, the present invention is not limited to the above-described preferred embodiment, but may be modified, changed, and substituted without departing from the technical scope of the present invention.

For instance, in the above-described preferred embodiment, the present invention was applied to the X-ray 3-D image display apparatus. Alternatively, the present invention may be applied to other 3-D image display apparatuses, for example, MR (magnetic resonance) 3-D image display apparatuses, wherein the scanning slice is diagnosed based upon the window level and width.

Furthermore, a zooming function may be utilized by operating the display mode changing key 12 mounted on the instruction unit 3, so that the desired 3-D image may be enlarged.

As previously described in detail, in the three-dimensional image display apparatus according to the present invention, since the region of the object's tissue to be imaged in the three-dimensional image may be successively changed e.g., from organs into outer skins, bones and blood vessels, by simply operating the positioning device such as a rotary encoder unit employed in the conventional imaging apparatus, the desirable 3-D image displays are immediately updated, which may cause the diagnostic functions of the 3-D image display apparatus to be improved.

What is claimed is:

1. A three-dimensional image display apparatus comprising:
   positioning means for determining a window value of a two-dimensional image of a biological body under medical examination, said positioning means including
      first rotary encoder/pulse counter circuit means for producing a first positioning signal indicating a center value within a threshold level range of a region of said biological body to be imaged, said first rotary encoder/pulse counter circuit means having
         a first rotary encoder having a first rotary knob, said first rotary encoder producing a first pulse train in response to a rotation of said first rotary knob,
         first and second D-type flip-flops, said first and second D-type flip-flops receiving said first pulse train produced by said first rotary encoder to produce a first count-up pulse and a first count-down pulse, respectively, and
         a first pulse counter, said first pulse counter receiving said first count-up pulse and said first count-down pulse to produce said first positioning signal, and
      second rotary encoder/pulse counter circuit means for producing a second positioning signal indicating an upper limit and a lower limit of said threshold level range, said second rotary encoder/pulse counter circuit means having
         a second rotary encoder having a second rotary knob, said second rotary encoder producing a second pulse train in response to a rotation of said second rotary knob,
         third and fourth D-type flip-flops, said third and fourth D-type flip-flops receiving said second pulse train produced by said second rotary encoder to produce a second count-up pulse and a second count-down pulse, respectively, and
         a second pulse counter, said second pulse counter receiving said second count-up pulse and said second count-down pulse to produce said second positioning signal;
   setting means for selecting a region of said biological body to be imaged as a three-dimensional image;
   three-dimensional image constructing means for constructing, in response to said window value, said three-dimensional image corresponding to said selected region of said biological body from data of a plurality of computerized tomographic images; and
   displaying means for displaying said three-dimensional image constructed by said three-dimensional image constructing means.

2. The three-dimensional image display apparatus as claimed in claim 1, further comprising:
   acquiring means for acquiring said plurality of computerized tomographic images to form said data of said plurality of tomographic images;
   storing means for storing said data of said plurality of computerized tomographic images; and
   means for sequentially reading out said data of said plurality of tomographic images from said storing means into said three-dimensional image constructing means.

3. The three-dimensional image display apparatus as claimed in claim 2, further comprising:
   work buffer memory means for temporarily storing said data of said plurality of tomographic images read out from said storing means; and
   display image buffer memory means for temporarily storing data of said three-dimensional image.

4. The three-dimensional image display apparatus as claimed in claim 1, wherein said three-dimensional image constructing means includes high-speed calculation unit means for performing at least a binary-coding operation, a voxel data calculation, a projection image conversion, and a distance image forming operation with respect to said data of said plurality of computerized tomographic images.

5. The three-dimensional image display apparatus as claimed in claim 4, wherein, while said high-speed calculation unit means constructs said three-dimensional image from said data of said plurality of computerized tomographic imagers, a binary-coded image is formed by said high-speed calculation unit means and simultaneously displayed with said three-dimensional image by said displaying means.

6. The three-dimensional image display apparatus as claimed in claim 1, wherein said three-dimensional image display apparatus is an X-ray three-dimensional image display apparatus, and said positioning means determines upper and lower limits of an X-ray computerized tomography value and a central X-ray computer tomography value between said upper and lower limits of said X-ray computerized tomography value.

7. The three-dimensional image display apparatus as claimed in claim 1, wherein said three-dimensional image display apparatus is a magnetic resonance three-dimensional image display apparatus, and said positioning means determines upper and lower limits of a magnetic resonance value and a central magnetic resonance value between said upper and lower limits of said magnetic resonance value.

* * * * *

UNITED STATES PATENT AND TRADEMARK OFFICE
CERTIFICATE OF CORRECTION

PATENT NO. : 5,229,935
DATED : July 20, 1993
INVENTOR(S) : Ichiro Yamagishi et al.

It is certified that error appears in the above-indentified patent and that said Letters Patent is hereby corrected as shown below:

Claim 5, column 6, line 63, change "imagers" to --images--.

Signed and Sealed this

Twenty-sixth Day of April, 1994

BRUCE LEHMAN

*Attest:*

*Attesting Officer*    *Commissioner of Patents and Trademarks*